US007585625B2

(12) United States Patent
de Rooij et al.

(10) Patent No.: US 7,585,625 B2
(45) Date of Patent: Sep. 8, 2009

(54) STORING AND DETECTING NUCLEIC ACID ADMINISTERED TO A SOLID CARRIER

(75) Inventors: Esther Regina de Rooij, Eemnes (NL); Marinus Petrus de Baar, Utrecht (NL)

(73) Assignee: PrimaGen Holding B.V., Amsterdam (NL)

( * ) Notice: Subject to any disclaimer, the term of this patent is extended or adjusted under 35 U.S.C. 154(b) by 0 days.

(21) Appl. No.: 10/817,164

(22) Filed: Apr. 1, 2004

(65) Prior Publication Data

US 2005/0074792 A1 Apr. 7, 2005

Related U.S. Application Data

(63) Continuation of application No. PCT/NL03/00491, filed on Jul. 3, 2003.

(51) Int. Cl.
*C12Q 1/68* (2006.01)
(52) U.S. Cl. .............................. 435/6; 435/5; 536/23.72
(58) Field of Classification Search ..................... 435/4, 435/6; 424/208.1, 280.1; 536/23.72
See application file for complete search history.

(56) References Cited

U.S. PATENT DOCUMENTS

| 5,482,834 | A | * | 1/1996 | Gillespie | ........................ 435/6 |
| 5,496,562 | A | | 3/1996 | Burgoyne | |
| 5,756,126 | A | | 5/1998 | Burgoyne | |
| 5,807,527 | A | | 9/1998 | Burgoyne | |
| 5,976,572 | A | | 11/1999 | Burgoyne | |
| 5,985,327 | A | | 11/1999 | Burgoyne | |
| 6,294,203 | B1 | | 9/2001 | Burgoyne | |
| 6,322,981 | B1 | | 11/2001 | Rodgers et al. | |
| 6,322,983 | B1 | | 11/2001 | Burgoyne | |
| 6,447,804 | B1 | | 9/2002 | Burgoyne | |
| 2002/0146696 | A1 | | 10/2002 | Burgoyne et al. | |

FOREIGN PATENT DOCUMENTS

WO    WO 98/23778    6/1998

OTHER PUBLICATIONS

Yourno et al. A Novel Polymerase Chain Reaction Method for Detection of Human Immunodeificiency Virus in Dried Blood Spots on Filter Paper, Journal of Clinical Microbiology, 1992, 30(11):2887-2892.*
Higuchi et al. Kinetic PCR analysis, Bio/Technology, 1993, 11:1026-1030.*
Romppanen et al. PC-Oligonucleotide Ligation Assay from Dried Blood Spots, Clinical Chemistry, 1999, 2022-2025 R.*
Boom et al. Rapid and Simple Method for Purification of Nucleic Acids, Journal of Clinical Microbiology, 1990, 28(3):495-503.*
de Baar et al. Single Rapid Real-Time Monitored Isothermal RNA Amplification Assay, Journal of Clinical Microbiology, 2001, 39(4):1378-1384.*
de Baar et al. One-Tube Real-Time Isothermal Amplification Assay, Journal of Clinical Microbiology, 2001, 39(5):1895-1902.*
Tzeng et al. An Effective Strategy of Using Molecular Testing to Screen Mentally Retarded Individuals for Fragile X Syndrome, Diagnostic Molecular Pathology, 2001, 10:34-40.*
Romppanen, E.-L. Oligonucleotide ligation assay: applications to molecular diagnosis of inherited disorders, Scand. J. Clin. Lab. Invest., 2001, 61:123-129.*
Caggana et al. Rapid, Efiicient Method for Multiplex Amplification from Filter Paper, Human Mutation, 1998, 11:404-409.*
PCT International Search Report, PCT/NL 03/00491 dated Nov. 4, 2003.
Phillips et al., "Detection of HIV-1 Viral RNA from Whole Blood Collected on Filter Paper," Abstracts of the interscience Conference on Antimicrobial Agents and Chemotherapy (41$^{st}$ Annual Meeting of the Interscience Conference on Antimicrobial Agents and Chemotherapy), Sep. 22-25, 2001, p. 354, vol. 41. Abstract.
O'Shea et al., "Use of dried whole blood spots for quantification of HIV-1 RNA," AIDS, Apr. 1, 1999, pp. 630-631, vol. 13, No. 5.
Nyambi et al., "Detection of Human Immunodeficiency Virus Type 1 (HIV-1) in Heel Prick Blood on Filter Paper from Children Born to HIV-1-Seropositive Mothers," Journal of Clinical Microbiology, Nov. 1994, pp. 2858-2860, vol. 32, No. 11.
Cassol et al., "Quantification of Human Immunodeficiency Virus Type 1 RNA from Dried Plasma Spots Collected on Filter Paper," Journal of Clinical Microbiology, Nov. 1997, pp. 2795-2801, vol. 35, No. 11.
Cassol et al., "Dried Bloods Spots Collected on Filter Paper: An International Resource for the Diagnosis and Genetic Characterization of Human Immunodeficiency Virus Type-1," Memorias do Instituto Oswaldo Cruz, May 1996, pp. 351-358, vol. 91, No. 3.
Moye et al., "Detection and Quantitation of HIV-1 RNA from Filter Paper Adsorbed Whole Blood or Plasma by NASBA Isothermal Amplification," 4$^{th}$ Conference on Retroviruses and Opportunistic Infections, 1997, Abstract.
Patisaul et al., Genistein Affects ERbeta- But Not ERalpha-Dependent Gene Expression in the Hypothalamus, Endocrinology, 2002, pp. 2189-2197, vol. 143, No. 6.
Protein Saver Cards (visited Mar. 25, 2009); <http://www.whatman.com/903ProteinSaverCards.aspx>.
U.S. Appl. No. 12/150,963, filed May 2, 2008, Penning et al., Methods for Using Mitochondrial Nucleic Acid for Determining a Health Status of an Individual.
U.S. Appl. No. 12/317,907, filed Dec. 29, 2008, Penning et al., Methods for Using Mitochondrial Nucleic Acid for Determining a Health Status of an Individual.

* cited by examiner

*Primary Examiner*—Stacy B Chen
(74) *Attorney, Agent, or Firm*—TraskBritt (57) ABSTRACT

The invention discloses a method for detecting a nucleic acid of interest in at least one sample comprising administering the sample to a solid carrier capable of at least in part absorbing the sample, drying the carrier, providing at least a representative part of the carrier to a nucleic acid isolation solution so that a representative amount of the nucleic acid is extracted from the carrier, and detecting the representative amount of the nucleic acid. With a method of the invention, a sample, such as a body fluid sample, is stabilized in such a way that it can be shipped from the site of taking (for instance local hospital or lab in a less-developed country) and be sent to a service testing laboratory elsewhere in the world by normal logistics means. At least 100 μl or at least 250 μl of sample is administered to the carrier in order to detect low titers of nucleic acid of interest. A kit for detecting, identifying and/or quantifying a nucleic acid of interest in a sample, comprising a solid carrier capable of at least in part absorbing the sample, and a nucleic acid isolation solution, is also described.

8 Claims, 2 Drawing Sheets

```
                       SEQUENCE LISTING

<160> NUMBER OF SEQ ID NOS: 4

<210> SEQ ID NO 1
<211> LENGTH: 47
<212> TYPE: DNA
<213> ORGANISM: Artificial sequence
<220> FEATURE:
<223> OTHER INFORMATION: primer P1

<400> SEQUENCE: 1
aattctaata cgactcacta tagggagagg ggcgccactg ctagaga              47

<210> SEQ ID NO 2
<211> LENGTH: 20
<212> TYPE: DNA
<213> ORGANISM: Artificial sequence
<220> FEATURE:
<223> OTHER INFORMATION: primer P2

<400> SEQUENCE: 2
ctcaataaag cttgccttga                                            20

<210> SEQ ID NO 3
<211> LENGTH: 32
<212> TYPE: DNA
<213> ORGANISM: Artificial sequence
<220> FEATURE:
<223> OTHER INFORMATION: primer, molecular beacon for the wild-type
      HIV-1 sequence, attached to FAM

<400> SEQUENCE: 3
cgacgtagta gtgtgtgccc gtctgtacgt cg                              32

<210> SEQ ID NO 4
<211> LENGTH: 35
<212> TYPE: DNA
<213> ORGANISM: Artificial sequence
<220> FEATURE:
<223> OTHER INFORMATION: primer, molecular beacon for the system control
      RNA MB054, attached to ROX

<400> SEQUENCE: 4
ccgactctct acacaccaga caaaaaacga gtcgg                           35
```

STORING AND DETECTING NUCLEIC ACID ADMINISTERED TO A SOLID CARRIER

CROSS-REFERENCE TO RELATED APPLICATIONS

This application is a continuation of PCT/NL2003/000491, filed Jul. 3, 2003, designating the United States of America, corresponding to PCT International Publication WO 2003/080869 (published in English on Oct. 2, 2003), the contents of the which are incorporated herein in its entirety.

TECHNICAL FIELD

The invention relates to the fields of biotechnology and medicine. More particularly, the invention relates to diagnosis. The invention further relates to detection and/or quantification of a nucleic acid of interest in a sample.

BACKGROUND

Infections with pathogens are commonly observed all over the world. Such infections include viral, bacterial, fungal and parasite infections. Early diagnosis of an infection is often preferred for efficient treatment, which can prevent severe pathological symptoms. Sometimes, early diagnosis is a prerequisite for a possibility of treatment, for extending a lifetime and/or for improving the quality of life. Examples of such infections comprise Hepatitis C virus, Hepatitis B virus, tuberculosis, malaria and HIV, such as HIV-1.

The HIV-1 epidemic spreads readily over the world and with the spread of the virus, the circulating subtypes of the HIV-1 virus are no longer restricted to one geographical place on earth. This development requires an application of (nucleic acid) diagnostic tests that can detect all subtypes of the HIV virus with equal accuracy and precision.

The globalization of the epidemic and, especially, the severity in resource-poor countries (sub-Saharan Africa and south-east Asia) has driven the developed world to assist the fighting of infection in the less-developed countries with access programs to pharmaceuticals. However, in order to efficiently help HIV-1 infected people in the less-developed world, there has to be suitable diagnostics in place to monitor the efficacy of a treatment. Such suitable diagnostics are especially viral load assays that measure the amount of HIV-1 RNA in a bodily fluid, such as blood, blood plasma, mother's milk, semen, lymph fluid, sputum, liquor, saliva and/or urine of infected individuals. Likewise, suitable nucleic acid load assays are desired for other infection-related diseases.

The current status of suitable nucleic acid load assays is of such a high technical standard that these are not easily transferred to areas located at considerable distance of technological resources such as in sub-Saharan Africa and/or south-east Asia. This requires significant investment in infrastructure that is impossible in the setting of these regions. An alternative solution is an analysis of patient samples in laboratories in the developed world (for instance Europe and north America). This alternative is, however, impossible to exercise due to logistic problems. Body fluid samples such as blood or blood plasma samples of individuals have to be shipped to the laboratory in frozen conditions at temperatures well below 0° C., usually in a box with dry ice. This way of sending clinical material is very expensive and requires the availability of dry ice at the place of shipment. The latter is often not the case in countries of the less-developed world. Because of the costs and the unavailability of dry ice the remote testing of samples in laboratories ("service testing") is not an option for these countries and for infected people in these countries. The pharmaceutical access programs for less-developed countries can only be successful if diagnosis is optimized.

SUMMARY OF THE INVENTION

The invention discloses a method for detecting a nucleic acid of interest in at least one sample, comprising: administering the sample to a solid carrier capable of at least in part absorbing the sample; drying the carrier; providing at least a representative part of the carrier to a nucleic acid isolation solution so that a representative amount of the nucleic acid is extracted from the carrier; and detecting the representative amount of the nucleic acid.

With a method of the invention, a sample, such as a body fluid sample, is stabilized in such a way that it can be shipped from the site of taking (for instance a local hospital or lab in a less-developed country) and be sent to a service testing laboratory elsewhere in the world by normal logistics means, for instance, by normal postal service. The method makes possible shipment of a dried sample via surface mail to a remote lab for detection of a nucleic acid of interest present in a sample.

A method of the invention can be performed with known techniques. For instance, a defined amount of liquid sample can be administered to a solid carrier using a pipette. The solid carrier can comprise any solid carrier known in the art, as long as it is capable of at least, in part, absorbing the sample. For instance, the solid sample can comprise silica. In another embodiment, the solid carrier comprises filter paper. A filter paper is capable of absorbing a liquid sample, while it is of light weight which is important for postal services. The filter paper can comprise plain untreated filter paper like the 903 paper from Schleicher and Schuell, or treated filter paper that immobilizes nucleic acid for rapid purification. Two examples in the field are IsoCode paper from Schleicher and Schuell or FTA-treated paper from Whatman, both of which are bactericidal, fungicidal and virucidal, inhibits the growth of bacteria and fungi, and kills viruses that come in contact with the matrix, allowing for safe sample handling and sample stability.

Another example of a suitable carrier to store and transport dried fluid samples is a device designed by Lifestock (U.S. Pat. No. 5,139,742) This device contains a small knife with a capillary tube directly attached to it, which enables collection, storage and transportation of blood that dries in the capillary tube, thereby, comparable to the method with the filter paper.

The carrier can be dried by different known techniques. In one embodiment, the sample is dried to the air which is inexpensive and effective.

By a representative part of a carrier is meant a part which is indicative for the amount of sample administered to the solid carrier. For instance, the representative part can comprise the whole of the sample. The representative part can also comprise half the amount of the sample. In that case, the other half can be used to perform a second experiment. The second experiment can be a different experiment, or can be a similar experiment. In the latter case, a certain result can be obtained in duplo, which is more accurate.

By a representative amount of nucleic acid is meant an amount which is indicative for the amount of nucleic acid present in the sample. The representative amount can comprise the whole amount of the nucleic acid present in the sample. Alternatively, the representative amount can comprise a part of the nucleic acid present in the sample.

In one embodiment, a method of the invention is disclosed wherein at least 100 µl of sample is administered to the carrier. In another embodiment, at least 250 µl of sample is administered to the carrier. In a further embodiment, at least 500 µl of sample is administered to the carrier. With a high sample volume, low titers of nucleic acids of interest can still be detected. A major drawback in current detection methods is that only nucleic acids with a concentration above a certain threshold value can be detected. This means that infected individuals with a low load of pathogenic nucleic acid are not diagnosed as being infected and, hence, do not get treatment at an appropriate early timepoint.

Until the present invention, high amounts of body fluid samples, such as blood or plasma samples, were not suitable for testing because inhibitory effects were observed. For instance, it has been reported that hemoglobin and carbonic anhydrase present in whole blood interfere with the polymerase chain reaction (4). PCR mixtures became deep brown because of the elution of heme and its degradation products from filter blotters (5). To improve a PCR amplification, specimens were treated with methanol before the PCR reaction (6). This involves an extra step, with a risk of contaminations and less reliable test results. Besides, chelating metal ions are reported to act as catalysts for the breakdown of DNA at a high temperature with low ionic strength (7).

Surprisingly, with a method of the invention high amounts of sample can be stored on a dried solid carrier and subsequently analyzed. None of the above-mentioned inhibitory effects of known techniques are observed and treatment with methanol as a precautionary measure is not necessary. With a method of the invention, it is possible to analyze large samples for the presence of a nucleic acid of interest. Hence, low concentrations of a nucleic acid of interest in a sample can be detected.

A method of the invention is suitable for screening individuals for the presence of one or more specific pathogens, such as HIV-1. Alternatively an individual suffering from a disease, or at risk of suffering from a disease, can be investigated with a method of the invention. Once one or more foreign nucleic acid(s) are found, it can be determined to which kind of microorganism it belongs. This can for instance be done by hybridization protocols using different kinds of probes. Alternatively, techniques to determine the sequence of the nucleic acid and analyzing this sequence for homology with any known sequences can be performed. In one embodiment, the invention discloses a method of the invention comprising identifying the nucleic acid of interest.

In yet another embodiment, a method of the invention is disclosed wherein the nucleic acid is quantified. Surprisingly, it is not only possible with a method of the invention to detect a nucleic acid of interest, but also to determine the amount of the nucleic acid present in the sample. With a method of the invention no significant amount of nucleic acid is lost/broken down during storage and/or during the isolation and/or detection procedure. In the example is shown that, if a method of the invention is used, a measured amount of a nucleic acid of interest from a dried sample stored on a solid carrier is comparable to the measured amount of the nucleic acid of interest when the sample is directly subjected to analysis.

Dried samples on a solid carrier can be investigated for the amount of pathogenic nucleic acid present. Hence, not only the presence, but also the stage of a disease can be determined. It is now possible to diagnose individuals of regions with insufficient facilities, such as inhabitants from resource-poor countries. A body fluid sample, such as a blood sample, can be collected on a solid carrier such as a filter paper. The filter paper can be sent to a laboratory, for instance in Western Europe. Subsequently, the amount of a nucleic acid of interest can be determined and, hence, the status of a disease. It can also be determined whether a treatment is effective by determining whether the amount of the nucleic acid declines over time.

In one aspect, the invention discloses a method wherein the solid carrier is provided with at least two samples. In another aspect, the samples are obtained from the same individual. In a further aspect, the samples are obtained from the same body fluid of the individual. The samples can, for instance, comprise two aliquots of blood. Each of the blood samples can be tested independently by a method of the invention. This way the presence and/or the amount of a nucleic acid of interest in the blood of the individual can be tested in duplo. This results in more accurate results. Moreover, each sample can be tested by different persons/different institutes. Errors made by individuals and/or errors because of unreliable equipment can be revealed by an independent second measurement.

In an alternative embodiment, the two samples are used for different purposes. For instance, one sample can be tested for the amount of viral nucleic acid, while the other sample can be tested for the amount of bacterial nucleic acid. Both samples can be used to obtain ratios between viral nucleic acid and chromosomal DNA (as is important for CMV), or for ratio between mitochondrial vs. cellular DNA/RNA, or to determine ratios involving mRNA's or ribosomal RNA's. Many of these tests, however, can also be carried out using only one sample.

In one embodiment, the solid carrier comprises a series of at least two samples taken at different time points. This way, a course of a disease can be followed over time. This embodiment is also suitable for determining whether a treatment is effective. For instance, a sample can be administered to the solid carrier at the start of a treatment, and at regular intervals afterwards. In this way, the solid carrier does not only serve the purpose of transportation device, but also for stable storage at ambient temperatures without degradation of the nucleic acid of interest. Such solid carrier can be sent to a suitable institute after a certain amount of time. It can be established whether a treatment is efficient by quantifying the amount of pathogenic nucleic acid in each sample by a method of the invention. It can be established whether the amount declines over time.

Likewise, samples can be taken from a diseased individual at regular intervals. The amount of pathogenic nucleic acid in each sample can be quantified. This provides more insight into the course of the disease; for instance whether the amount of pathogenic nucleic acid increases over time, etc.

It is not necessary to send each sample separately to the institute. A number of them can be collected over time and be sent at once. This saves time and money. Moreover, because the samples are sent together, no storing and sorting of separately sent samples is necessary. A risk of samples getting lost is decreased.

To even more accurately quantify an amount of a nucleic acid of interest with a method of the invention, a known amount of a reference nucleic acid can be administered to the solid carrier. The reference nucleic acid can be quantified, as well as a nucleic acid of interest. The accuracy of a quantification of a nucleic acid of interest can be determined by comparing a measured amount of the reference nucleic acid with the administered amount of the reference nucleic acid. If the measured amount differs slightly from the administered amount, the same is likely to be true for the nucleic acid of interest. Hence, a measured amount of the nucleic acid of interest can be corrected to obtain an even more accurate result.

Moreover, with a reference nucleic acid, a representative part comprising a part of a sample can be determined. If a representative part comprising a part of the sample is provided to the nucleic acid isolation buffer, and the measured amount of reference nucleic acid appears to be one third of the administered amount, it indicates that the measured amount of a nucleic acid of interest is also approximately one third of the amount present in the sample. Hence, a reference nucleic acid shows with which factor a measured amount of nucleic acid of the invention should be multiplied if a part of the sample is provided to the nucleic acid isolation buffer.

In one embodiment, a reference nucleic acid which spreads along the solid carrier essentially the same way as the nucleic acid of interest is disclosed. In that case it makes no significant difference which part of the solid carrier is used in a method of the invention. Another way of accurately quantifying the nucleic acid of interest is by relating it to the amount of other nucleic acids. In this way it is possible, in either the same reaction or in separate reactions, in either the same sample or one of the other samples, to establish a ratio between any DNA and DNA, any RNA and DNA or vice-versa, and any RNA and RNA target. The invention could comprise applications to determine the ratio between nucleic acids from the host, e.g., the amount of mitochondrial DNA versus nuclear DNA as a measure of response to certain HIV therapy, or between nucleic acids from a pathogen versus those from the host, e.g., the amount of CMV DNA versus host nuclear DNA. Other applications could comprise the amount of mRNA per cell within the field of gene expression profiling.

The invention also discloses a method of the invention wherein the representative part comprises the whole of the at least one sample. It is shown herein that even with a large sample, a reliable detection and/or quantification of a nucleic acid of interest is possible with a method of the invention. If the whole of a large sample is used, even low concentrations of nucleic acid can be detected and quantified.

A representative part of the carrier can be provided by cutting a visible spot out of a solid carrier such as filter paper. This cutting can be done using a normal pair of scissors, but can also be completely automated, e.g., using equipment from Wallack to punch out equal surfaces of the solid carrier. Another way of effectuating this type of punching by hand, would be to pre-punch the solid carrier, after which the sample is applied and dried. At arrival in the laboratory for analysis, this pre-punched part can be easy punched out completely by either specially designed devices or existing devices such as a Safe-lock tube from Eppendorf. Also a representative part of the spot can be used. However, in one embodiment, the whole carrier is used, as it is ensured that the whole sample is measured. According to the present invention, a solid carrier such as filter paper does not significantly influence a detection and/or quantification of a nucleic acid of interest. Therefore, a method of the invention is preferred wherein the representative part comprises essentially the whole of the solid carrier.

If in a method of the invention the solid carrier is provided with at least two samples, the representative part comprises one of the samples. The representative part can be used for detecting and/or quantifying a nucleic acid of interest. As has been explained herein, a representative part comprising the second sample can be used for a measurement in duplo. Alternatively, another measurement can be performed.

In one aspect, a method of the invention is disclosed wherein the nucleic acid isolation solution comprises a chaotropic nucleic acid isolation lysis buffer. In another embodiment, a nucleic acid isolation buffer as described by Boom et al is used. The solid carrier may comprise filter paper, since filter paper is cheap, well capable of absorbing a liquid sample and of light weight which facilitates transport. Typically, elution of the nucleic acid takes at least 30 minutes at room-temperature, or even shorter at elevated temperatures, whereas nucleic acid from a bodily fluid that is applied directly to the lysis buffer is typically released within 10 minutes. Elevated temperatures will facilitate efficient and quick elution of the nucleic acid from the solid carrier.

A method of the invention is suitable for detecting viral nucleic acid, such as retroviral nucleic acid. Viral nucleic acid can be present in a latent stage, which can last for a considerable time. Moreover, a virus such as HIV, HTLV and HHV is often present during a considerable time within an individual before the individual experiences any significant symptoms. During that time, the virus is often already transmittable to other persons. Moreover, treatment in an early stage can improve a chance of recovery, prolong a life-time and/or improve the quality of life. Therefore, it is particularly important to check an individual for the presence of viral nucleic acid with a method of the invention. Viral nucleic acids that may be detected include sequences from Hepatitis A, B, C, parvovirus, etc. In one embodiment, the viral nucleic acid comprises HIV and/or HTLV. In other embodiments, the viral nucleic acid comprises HIV-1.

In one embodiment, a method of the invention is disclosed, wherein the method comprises genotyping a mutant. This is useful for organisms with a fast-changing genome, such as (retro)viruses. Genotyping is useful for determining whether a certain treatment is likely to be suitable for an individual patient. Moreover, if a new mutant is found, an existing pharmaceutical preparation can be adapted, or a new medicament can be developed.

A method of the invention is suitable for detecting a nucleic acid of interest in a body fluid, such as blood, plasma, mother's milk, semen, lymph fluid, serum, sputum, liquor, saliva, and/or urine. A sample of such body fluid is easy to obtain and obtaining such sample does not cause much inconvenience to an individual, which would be the case if for instance a biopsy were taken. Moreover, obtaining a body fluid sample does not require special equipment, which is often lacking in less developed countries and in remote areas.

In one embodiment, a method of the invention is disclosed wherein the sample comprises a droplet of whole blood from a finger or heel puncture. Such finger or heel puncture is commonly taken from newborns, so that the material is often available without further bothering the individuals. In another embodiment, the sample is a plasma sample. A plasma sample allows more accurate measurement of an amount of free virus particles, whereas for instance a blood sample also includes viral nucleic acid integrated within cells. Measurement of free virus particles, essentially without viral nucleic acid integrated within cells, is particularly indicative for characteristics such as viral virulence, viral spread, etc. Hence, a plasma sample is may be used if such characteristics are to be determined.

To make sure that at least the minimally necessary amount of bodily fluids is collected, a pre-determined surface can be printed or applied in any other way to the solid carrier. The meaning is that the surface will be completely filled with the requested bodily fluid. Since an equal volume of whole blood will result in a smaller covered surface than a similar amount of bodily fluids, e.g., serum, or mother's milk, it may be necessary to have several surfaces printed for various bodily fluids on the same solid carrier, or to have carriers designed specifically for certain bodily fluids. In this way, it is ensured that minimally the correct amount of bodily fluid is collected.

For detection of a nucleic acid of interest, often an amplification step (such as PCR or NASBA) may be used. Amplified nucleic acid can be detected using known methods. A method of the invention therefore comprises an amplification step. In one embodiment, the amplification comprises real-time monitored amplification. Produced nucleic acid is made visible during such amplification reaction. This can be achieved by molecular beacon probes or other types of probes. Once these probes anneal to a template, a fluorescence signal can be generated which can be monitored during an amplification reaction. The intensity of fluorescence is indicative for the amount of nucleic acid generated. A calibration curve can be created using known amounts of nucleic acid. A fluorescence signal from a sample with an unknown amount of nucleic acid can be compared with the calibration curve. This way the amount of the nucleic acid in the sample can be determined, because the intensity of fluorescence and the amount of nucleic acid are correlated.

In another embodiment the nucleic acid detection and/or quantification is performed with an end-point read-out system. Such systems may comprise a colorimetric detection, an enzymatic assay, and/or a dipstick.

The invention also discloses a use of a dried solid carrier provided with a sample for detecting, identifying and/or quantifying a nucleic acid of interest in the sample. As has been described herein, the dried solid carrier can be stored and transported easily, after which reliable nucleic acid detection and quantification can be carried out. In one embodiment, the solid carrier comprises at least the equivalent of 100 µl of blood or a derivative thereof in dried form. The carrier may also comprise at least 250 µl, or at least 500 µl of blood or a derivative thereof in a dried form.

With a use of the invention, a large volume of sample can be investigated, allowing detection and/or quantification of a low concentration of nucleic acid. With a derivative of blood is meant at least part of a component of blood, such as serum and/or plasma. Blood which has been modified artificially is also within the scope of a derivative of blood. The way the solid carrier is designed, the carrier could contain the carrier itself that can absorb the bodily fluid, linked to a part of paper or surface on which information can be written or printed, e.g., information about the patient, date of sampling or more dates of sampling, therapy regimen, barcodes, ID-numbers, etc. Such a surface for this type of information is unequivocally linked at the carrier with sample, thereby making sure the information is not lost. Typically, this type of surface can contain much more information than a tube can hold. Logically, any variation on this theme is possible.

The invention also comprises a kit of parts for detecting, identifying and/or quantifying a nucleic acid of interest in a sample, comprising: a solid carrier capable of at least in part absorbing the sample; and a nucleic acid isolation solution.

In one embodiment, the kit further comprises means for nucleic acid amplification. The means may comprise means for real-time monitored amplification, and/or means for amplification with end-point detection/quantification. A kit of parts of the invention is useful in resource-poor countries with a few hospitals. Such hospitals can distribute the solid carriers, such as filter papers, among inhabitants in remote areas. Once samples have been collected, they can be stored and transported to such hospitals. If the hospital is properly equipped, the samples can be investigated using the nucleic acid isolation solution. Of course, also hospitals in developed countries can use a kit of part of the invention for collecting and testing a sample.

A kit of parts for detection, identification and/or quantification may contain a collection of materials necessary to safely draw the bodily fluid from the patient. Logically with external bodily fluids like urine, mother's milk or saliva, other safety precautions may be taken than when internal bodily fluids are samples like blood, plasma, serum, or lymph drain. For the internal bodily fluids, one can compose a kit that contains a solid carrier capable of at least in part absorbing the sample, and a nucleic acid isolation solution, next to a pair of examination gloves, a alcohol swab to clean the skin, a finger or heel puncture device, a bandage, an envelope, e.g., with the address of the destinated laboratory as well as with a space for an identification number or patient code, and coated inside for safe postal transportation, and a desiccator to keep the sample dry and to prevent it from fungal or bacterial growth. Other possibilities for the collection device could comprise specially designed devices for one-time use, like a device described in U.S. Pat. No. 5,139,742: Disposable liquid testing device by Livestock Control Holding B.V. in Amersfoort, the Netherlands. Any combination of these items, or replaced for other type of items/devices to be used for storage and/or transportation of any nucleic acid containing bodily fluids is possible.

A solid carrier comprising at least the equivalent of 500 µl of blood or a derivative thereof in dried form is also herewith discloses. In one embodiment, the solid carrier comprises at least two samples. If the samples are of the same kind, the samples can both be tested separately, resulting in an in duplo test. Furthermore, a result of a first test can be controlled by independently testing the other sample. Alternatively, the samples are used for different purposes.

A solid carrier of the invention comprising a series of samples obtained at different data is also herewith provided. As has been described before, such solid carrier is suitable for following a course of a disease over time, and/or for testing whether a certain treatment is effective. In one embodiment, a solid carrier of the invention comprises a known amount of a reference nucleic acid.

The invention is further explained in the following examples. The examples serve to clarify the invention and do not limit the scope of the invention in any way. Alternative embodiments are also within the scope of the present invention.

BRIEF DESCRIPTION OF THE FIGURES

FIG. 2. Comparison of quantitative HIV-1 data obtained on plasma samples that were analyzed directly or were first spotted and dried on filter paper. The assay lower limit of detection is at log2, indicated by solid lines in the graph. The

DETAILED DESCRIPTION

EXAMPLES

Example 1

Blood and blood plasma were spotted in 50 μl droplets on S&S 903 paper (Schleicher & Schull) and dried in the air. Simultaneously, 200 μl of the same blood and plasma samples were directly added to the lysis buffer as described by Boom et al. (1990). After drying, the spots on the filter paper were kept at ambient temperature for up to 3 weeks and may be kept at ambient temperature for months. The spots on the filter paper were excised with a normal pair of scissors and administered to a tube containing lysis buffer as described by Boom et al. (1990). The filter spots of 50 μl blood or plasma were added to three different tubes: 1) a 50 ml tube containing 9 ml lysis buffer, 2) a 15 ml tube containing 15 ml lysis buffer or 3) a 1.5 ml eppendorf tube containing 1 ml lysis buffer.

The tubes were mildly shaken on a shaking platform for 3 hours at ambient temperature. During this incubation, the blood or plasma spot dissolves from the filter paper into the lysis buffer. The filters were removed from the tubes with a cleaned pair of tweezers. Between tubes, the tweezers were cleaned with hot water-chlorine-hot water-70% alcohol.

To the tubes with lysis buffer and the samples a $1 \cdot 10^6$ copies of a system control RNA molecule were added to allow identification of false negative reactions at a later stage. The system control RNA is amplified with the same primers as the wild-type HIV-1 and detected with a distinguishable probe in the reaction. Due to a length difference, the system control RNA can be amplified and detected in the absence (or very low amounts) of the wild-type HIV-1 RNA.

The nucleic acid present in the lysis buffer was further purified with the method described by Boom et al (1990) or with dedicated isolation kits purchased from Qiagen (Qiagen GmbH, Max Volmer Strasse 4, 40724 Hilden, Germany) or Biomerieux (formerly Organon Teknika, Boseind 15, 5281 RM Boxtel, The Netherlands) and used according to the manufacturer's protocols. The isolated nucleic acid was stored at −80° C. until further analysis. Usually 5 μl was used as input in NASBA amplification reactions determining the amount of HIV-1 RNA as described by De Baar et al. (1, 2).

Standard NASBA nucleic acid amplification reactions were performed in a 20 μl reaction volume and contained: 40 mM Tris-pH 8.5, 70mM KCl, 12 mM $MgCl_2$, 5 mM dithiotreitol, 1 mM dNTP's (each), 2 mM rNTP's (each), 0.2 μM primer (each), (P1: AAT TCT AAT ACG ACT CAC TAT AGG GAG AGG GGC GCC ACT GCT AGA GA (SEQ ID NO: 1) and P2: CTC AAT AAA GCT TGC CTT GA) (SEQ ID NO: 2), 0.05 μM molecular beacon for the wild-type HIV-1 sequence (MB045: FAM-CGA CGT AGT AGT GTG TGC CCG TCT GTA CGT CG-dabcyl) (SEQ ID NO: 3), 0.05 μM molecular beacon for the system control RNA MB054: ROX-CCG ACT CTC TAC ACA CCA GAC AAA AAA CGA GTC GG-dabcyl) (SEQ ID NO: 4).

0.05 μM molecular beacon for the wild-type HIV-1 sequence, 0.05 μM molecular beacon for the system control RNA, 375 mM sorbitol, 0.105 μg/μl bovine serum albumin, 6.4 units AMV RT, 32 units T7 RNA polymerase, 0.08 units RNase H and input nucleic acid. The complete mixture, except the enzymes was, prior to adding the enzymes, heated to 65° C. in order to denature any secondary structure in the RNA and to allow the primers to anneal. After cooling the mixture to 41° C., the enzymes were added. The amplification took place at 41° C. for 90 min in a thermostated fluorimeter (CytoFluor 2000 or EasyQ Reader) and the fluorescent signal of the molecular beacon probe was measured every minute.

To achieve quantification, a dilution series of target sequence for a particular primer set was amplified and the time points at which the reactions became positive (the time to positivity, TTP) were plotted against the input amounts of nucleic acid. This way a calibration curve was created that could be used to read TTP values of reactions with unknown amounts of input and deduce the input amount.

The results of the determinations in example 1 are shown in Table 1 below. By the results of the system control RNA is appeared that there were no false negative results and all negative data reported in Table 1 are true negative data resulting from the absence of HIV-1 sequence or presence at concentrations below the detection limit of the tests.

| Patient # | 200 μl plasma direct to lysis buffer[A] | 200 μl blood direct to lysis buffer[B] | 50 μl plasma spotted[B] | 200 μl plasma spotted[A] | 50 μl blood spotted[B] | 200 μl blood spotted[A] |
|---|---|---|---|---|---|---|
| R02-05195 | Neg. | Pos. | Neg. | Neg. | Neg. | LQL |
| R02-05260 | Neg. | Neg. | Neg. | Neg. | Neg. | Neg. |
| R02-05179 | 3.84 | Pos. | Pos. | 3.86 | Pos. | 3.86 |
| R02-05183 | LQL. | Pos. | Pos. | 3.74 | Pos. | LQL |
| R02-05240 | 3.79 | Pos. | Pos. | 3.86 | Pos. | 3.77 |
| R02-05244 | 3.79 | Pos. | Pos. | 3.59 | Pos. | LQL |
| R02-05265 | 3.20 | Pos. | Neg. | LQL | Pos. | LQL |
| R02-05175 | 5.18 | Pos. | Pos. | 4.79 | Pos. | 4.76 |

[A]The results were determined quantitatively as described in the text with TTP measurements. The results are given as the Log number. Neg. indicates a negative result, LQL indicates a positive result, but too low for accurate quantification
[B]The determinations of 200 μl blood direct to lysis buffer, 50 μl plasma spotted and 50 μl blood spotted were not performed quantitatively, only qualitative with either a positive (Pos.) or negative (Neg.) result.

The data in Table 1 indicate a good correlation between the results obtained with the direct admission of sample to the lysis buffer compared to first spotting of the sample on paper, drying and thereafter admission to the lysis buffer.

Example 2

Mother milk of 1 woman, spiked with virus from 6 different isolates in 4 concentrations was spotted in 4 times 50 μl droplets on S&S 903 paper (Schleicher & Schuell), dried on the air and stored for a minimum of one week at ambient temperature. After drying, the spots on the filter paper were kept at ambient temperature for up to 3 weeks and may be kept at ambient temperature for months. Simultaneously, 200 µl of the same mother milk samples was directly added to the lysis buffer as described by Boom et al. (1990). The spots on the filter paper were excised with a normal pair of scissors and administered to a tube containing 4 ml lysis buffer as described by Boom et al. (1990).

The tubes were mildly shaken on a shaking platform overnight at ambient temperature. During this incubation the dried spot dissolves from the filter paper into the lysis buffer. Subsequently, the filters were removed from the tubes with a cleaned pair of tweezers. Between tubes the tweezers were subsequently cleaned with chlorine-hot water-70% alcohol.

To the tubes with lysis buffer and sample 1,000,000 copies of a system control RNA molecule was added to allow identification of false negative reactions at a later stage. The system control RNA is amplified with the same primers as the wild-type HIV-1 and detected with a distinguishable probe in the reaction. Due to a length difference, the system control RNA can be amplified and detected in the absence (or very low amounts) of the wild-type HIV-1 RNA. The nucleic acid now present in the lysis buffer was further purified with the method described by Boom et al (1990) or with dedicated isolation kits purchased from Qiagen (Qiagen GmbH, Max Volmer Strasse 4, 40724 Hilden, Germany) or Biomerieux (formerly Organon Teknika, Boseind 15, 5281 RM Boxtel, The Netherlands) and used according to the manufacturer's protocols. The isolated nucleic acid was stored at −80° C. until further analysis. Usually 5 µl was used as input in NASBA amplification reactions determining the amount of HIV-1 RNA as described by De Baar et al.

Standard NASBA nucleic acid amplification reactions were performed in a 20 µl reaction volume and contained: 40 mM Tris-pH 8.5, 70 mM KCl, 12 mM $MgCl_2$, 5 mM dithiotreitol, 1 mM dNTP's (each), 2 mM rNTP's (each), 0.2 µM primer (each) (P1: AAT TCT AAT ACG ACT CAC TAT AGG GAG AGG GGC GCC ACT GCT AGA GA (SEQ ID NO: 1) and P2: CTC AAT AAA GCT TGC CTT GA) (SEQ ID NO: 2), 0.05 µM molecular beacon for the wild-type HIV-1 sequence (MB045: FAM-CGA CGT AGT AGT GTG TGC CCG TCT GTA CGT CG-dabcyl) (SEQ ID NO: 3), 0.05 µM molecular beacon for the system control RNA (MB054: ROX-CCG ACT CTC TAC ACA CCA GAC AAA AAA CGA GTC GG-dabcyl) (SEQ ID NO: 4), 375 mM sorbitol, 0.105 µg/µl bovine serum albumin, 6.4 units AMV RT, 32 units T7 RNA polymerase, 0.08 units RNase H and input nucleic acid. The complete mixture, except the enzymes was, prior to adding the enzymes, heated to 65° C. in order to denature any secondary structure in the RNA and to allow the primers to anneal. After cooling the mixture to 41° C., the enzymes were added. The amplification took place at 41° C. for 60 min in a thermostated fluorimeter (CytoFluor 2000 or EasyQ Reader) and the fluorescent signal of the molecular beacon probe was measured every minute.

To achieve quantification, a dilution series of target sequence for a particular primer set was amplified and the time points at which the reactions became positive (the time to positivity, TTP) were plotted against the input amounts of nucleic acid. This way a calibration curve was created that could be used to read TTP values of reactions with unknown amounts of input and deduce the input amount.

Figure 1:
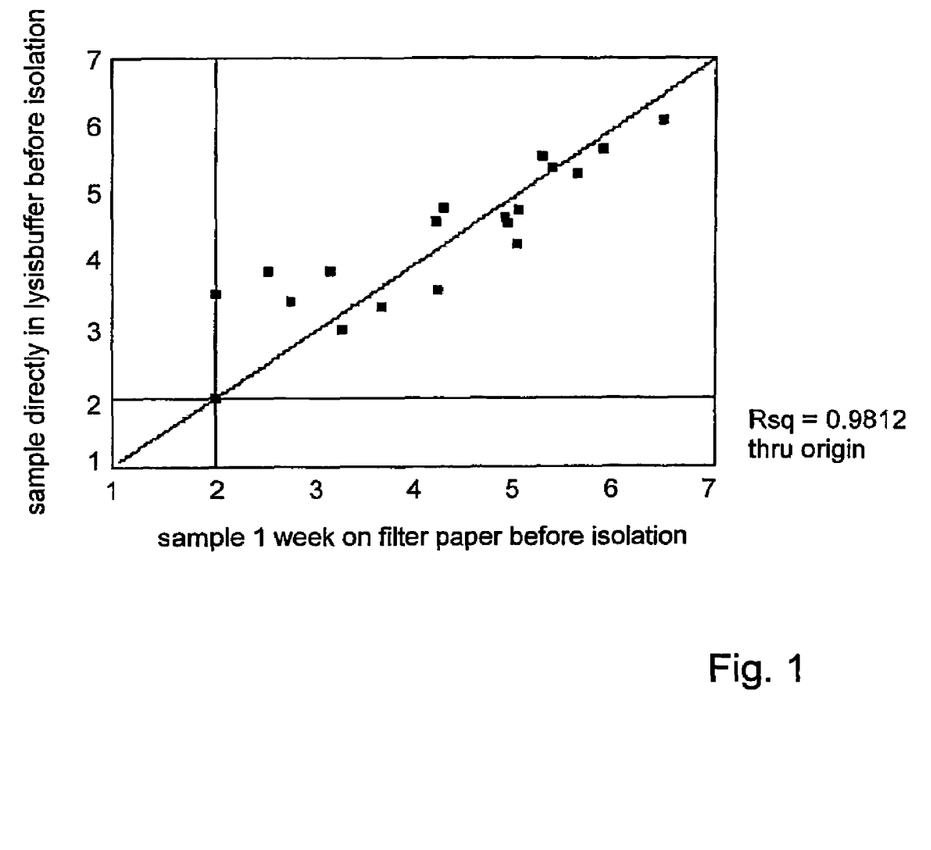
FIG. 1. Comparison of quantitative HIV-1 data obtained on mother milk samples that were analyzed directly or were first spotted and dried on filter paper. The assay cut of is at log2, indicated by solid lines in the graph. The numbers on the axis indicates the log copy number of HIV-1 RNA molecules found in the test. The data in FIG. 1 indicates a very good correlation between the results obtained with the direct admission of sample to the lysis buffer compared to first spotting of the sample on paper, drying and thereafter admission to the lysis buffer.

The results of the determinations of the same samples spotted and added directly to the lysis buffer were compared and the analysis is shown in FIG. 1 below. By the results of the system control RNA, it appeared that there were no false negative results and all negative data reported in FIG. 1 are true negative data resulting from the absence of HIV-1 sequence or presence at concentrations below the detection limit of the tests.

Example 3

Plasma of 88 HIV-1 infected individuals was spotted in 200 µl droplets on S&S 903 paper (Schleiger & Schull) and dried in the air and stored for a minimum of 24 hours at ambient temperature. Simultaneously, 200 µl of the same plasma samples was directly added to the lysis buffer as described by Boom et al. (1990). The spots on the filter paper were pinched out and administered to a tube containing 4 ml lysis buffer as described by Boom et al. (1990).

The tubes were mildly shaken on a shaking platform for 3 hours at ambient temperature. During this incubation the dried spot dissolves from the filter paper into the lysis buffer. Subsequently the filters were removed from the tubes with a cleaned pair of tweezers. Between tubes the tweezers were subsequently cleaned with hot water-chlorine-hot water-70% alcohol.

The nucleic acid now present in the lysis buffer was further purified with the method described by Boom et al (1990) or with dedicated isolation kits purchased from Qiagen (Qiagen GmbH, Max Volmer Strasse 4, 40724 Hilden, Germany) or Biomerieux (formerly Organon Teknika, Boseind 15, 5281 RM Boxtel, The Netherlands) and used according to the manufacturer's protocols. The isolated nucleic acid was stored at −80° C. until further analysis. Usually 5 µl was used as input in NASBA amplification reactions determining the amount of HIV-1 RNA as described by De Baar et al [2,3].

Standard NASBA nucleic acid amplification reactions were performed in a 20 µl reaction volume and contained: 40 mM Tris-pH 8.5, 70 mM KCl, 12 mM $MgCl_2$, 5 mM dithiotreitol, 1 mM dNTP's (each), 2 mM rNTP's (each), 0.2 µM primer (each), 0.05 µM molecular beacon for the wild-type HIV-1 sequence, 0.05 µM molecular beacon for the system control RNA, 375 mM sorbitol, 0.105 µg/µl bovine serum albumin, 6.4 units AMV RT, 32 units T7 RNA polymerase, 0.08 units RNase H and input nucleic acid. The complete mixture, except the enzymes was, prior to adding the enzymes, heated to 65° C. in order to denature any secondary structure in the RNA and to allow the primers to anneal. After cooling the mixture to 41° C., the enzymes were added. The amplification took place at 41° C. for 90 min in a thermostated fluorimeter (CytoFluor 2000 or EasyQ Reader) and the fluorescent signal of the molecular beacon probe was measured every minute.

To achieve quantification, a dilution series of target sequence for a particular primer set was amplified and the time points at which the reactions became positive (the time to positivity, TTP) were plotted against the input amounts of nucleic acid. This way a calibration curve was created that could be used to read TTP values of reactions with unknown amounts of input and deduce the input amount.

Figure 2:
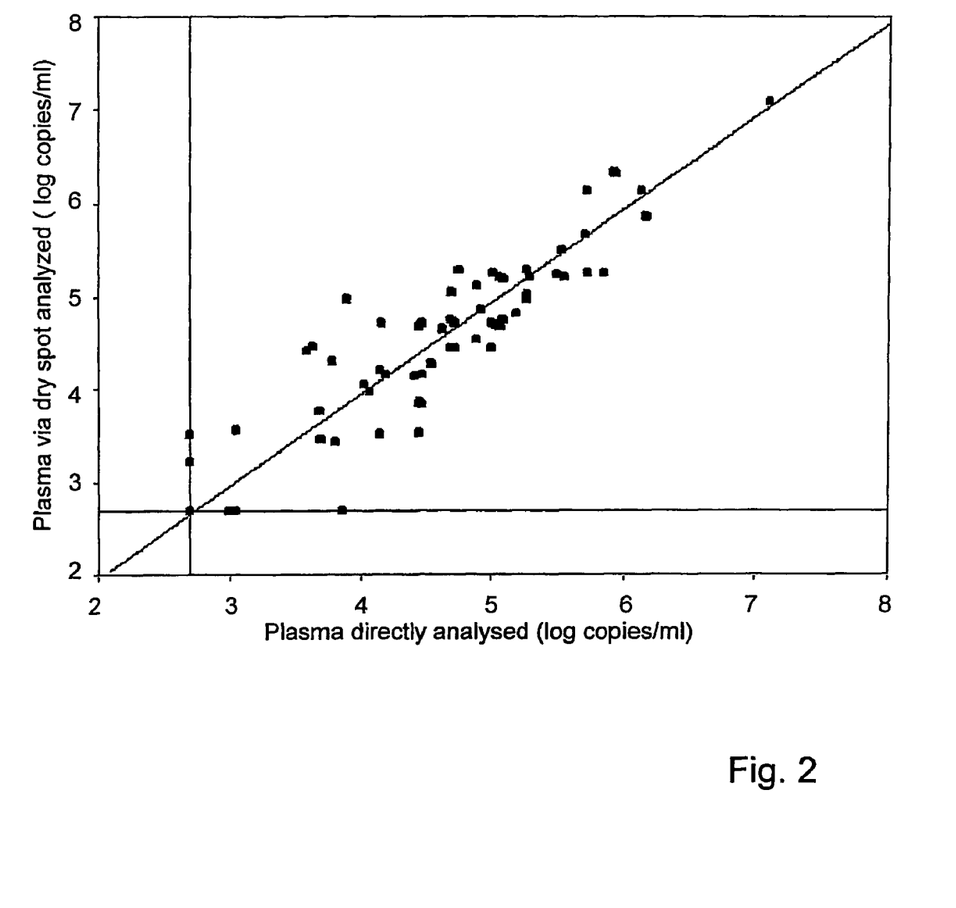

The results of the determinations of the same samples spotted and added directly to the lysis buffer were compared and the analysis is shown in FIG. 2.

The data in FIG. 2 indicate a very good correlation between the results obtained with the direct admission of sample to the lysis buffer compared to first spotting of the sample on paper, drying and thereafter admission to the lysis buffer. When analyzed with the Pearson correlation test a correlation coefficient (r) of 0.919 for plasma direct and 0.959 for dried plasma was found.

REFERENCES

1. Boom R, Sol C J, Salimans M M, Jansen C L, Wertheim-van Dillen P M, van der Noordaa J, 1990. Rapid and simple method for purification of nucleic acids. J Clin Microbiol; 28(3):495-503.
2. de Baar M P, van Dooren M W, de Rooij E, Bakker M, van Gemen B, Goudsmit J, de Ronde A. Single rapid real-time monitored isothermal RNA amplification assay for quantification of human imnmunodeficiency virus type 1 isolates from groups M, N, and O. J Clin Microbiol. 2001 April; 39(4): 1378-84.
3. de Baar M P, Timmermans E C, Bakker M, de Rooij E, van Gemen B, Goudsmit J. One-tube real-time isothermal amplification assay to identify and distinguish human immunodeficiency virus type 1 subtypes A, B, and C and circulating recombinant forms AE and AG. J Clin Microbiol. 2001 May; 39(5):1895-902.
4. Caggana M, Conroy J, Pass K. Rapid, efficient method for multiplex amplification from filter paper. Human mutation 1998; 11: 404-409.
5. Romppanen E, Mononen I. PCR-oligonucleotide ligation assay from dried blood spots. Clinical Chemistry 1999; 45(11): 2022-2025.
6. Romppanen E. Oligonucleotide ligation assay: applications to molecular diagnosis of inherited disorders. Scand J Clin Lab Invest 2001; 61: 123-130.
7. Tzeng C C, Lin S J, Chen Y J, Kuo P L, Jong Y J, Tsai L P, Chen R M. An effective strategy of using molecular testing to screen mentally retarded individuals for fragile X syndrome. Diagnostic Molecular Pathology 2001; 10: 34-40.

What is claimed is:

1. A process for preparing at least one sample for a method of detecting and quantifying a total amount of HIV nucleic acid present in the at least one sample, said process comprising:
   a) administering at least 100 microliters of the at least one sample to a piece of filter paper capable of absorbing the at least one sample, wherein the absorption results in at least one spot comprising at least 100 μL of the at least one sample on the filter paper,
   b) drying the filter paper having the absorbed at least one spot comprising at least 100 μL of the at least one sample,
   c) storing the filter paper for at least one week,
   d) excising the at least one spot comprising at least 100 μL of the at least one sample from the surrounding filter paper,
   e) extracting nucleic acid from all of the at least one spot comprising at least 100 μL of the at least one sample with a chaotropic nucleic acid isolation solution,
   f) detecting HIV nucleic acid, if present, and
   g) quantifying the total amount of the HIV nucleic acid present in the at least one sample.

2. The process according to claim 1, wherein at least 200 μl of the at least one sample is administered to the filter paper.

3. The process according to claim 2, wherein at least 250 μl of the at least one sample is administered to the filter paper.

4. The process according to claim 1, wherein at least two samples are administered to the filter paper.

5. The process according to claim 1, further comprising administering a known amount of a reference nucleic acid to the filter paper.

6. The process according to claim 1, wherein the HIV nucleic acid is from HIV-1.

7. A process for detecting an RNA of interest in at least one sample, the process comprising:
   administering at least 250 μl of the at least one sample and a known amount of a reference nucleic acid to a solid carrier capable of absorbing the at least one sample;
   drying the solid carrier;
   extracting at least 100 μL of the at least one sample from the solid carrier with a nucleic acid isolation solution; and
   detecting the RNA of interest, if present, in the representative part of the at least one sample.

8. The process according to claim 7, wherein at least 500 μl of the at least one sample is administered to said carrier.

* * * * *